United States Patent
Beger et al.

(10) Patent No.: US 9,795,417 B2
(45) Date of Patent: Oct. 24, 2017

(54) PEDICLE SCREW SYSTEM AND SPINAL STABILIZATION SYSTEM

(71) Applicant: Aesculap AG, Tuttlingen (DE)

(72) Inventors: Jens Beger, Tuttlingen (DE); Claudia Stoerk, Emmingen (DE); Sven Krüger, Trossingen (DE)

(73) Assignee: Aesculap AG (DE)

( * ) Notice: Subject to any disclaimer, the term of this patent is extended or adjusted under 35 U.S.C. 154(b) by 43 days.

(21) Appl. No.: 14/948,905

(22) Filed: Nov. 23, 2015

(65) Prior Publication Data
US 2016/0143668 A1    May 26, 2016

(30) Foreign Application Priority Data

Nov. 24, 2014  (DE) .......................... 10 2014 117 176

(51) Int. Cl.
*A61B 17/70*    (2006.01)

(52) U.S. Cl.
CPC ...... *A61B 17/7037* (2013.01); *A61B 17/7032* (2013.01); *A61B 17/7077* (2013.01)

(58) Field of Classification Search
CPC ............ A61B 17/7032; A61B 17/7037; A61B 17/7077
See application file for complete search history.

(56) References Cited

U.S. PATENT DOCUMENTS

| | | | | |
|---|---|---|---|---|
| 5,020,519 A | * | 6/1991 | Hayes ................. | A61B 17/025 600/226 |
| 5,364,397 A | * | 11/1994 | Hayes .................... | A61B 17/88 606/1 |
| 5,707,371 A | * | 1/1998 | Metz-Stavenhagen | A61B 17/861 606/104 |
| 6,440,133 B1 | * | 8/2002 | Beale ................. | A61B 17/7086 606/104 |
| 6,551,316 B1 | * | 4/2003 | Rinner .............. | A61B 17/8866 606/205 |
| 6,648,888 B1 | * | 11/2003 | Shluzas ............. | A61B 17/7091 606/86 A |

(Continued)

FOREIGN PATENT DOCUMENTS

| | | |
|---|---|---|
| DE | 9202587 | 4/1992 |
| DE | 102011053295 | 3/2013 |

(Continued)

*Primary Examiner* — Ellen C Hammond
*Assistant Examiner* — Stuart S Bray
(74) *Attorney, Agent, or Firm* — RatnerPrestia

(57) ABSTRACT

A pedicle screw system, including a pedicle screw having a screw shaft with an external thread and having a screw head supported on the screw shaft in a ball-and-socket joint relationship. The screw head includes a connecting element receptacle for a connecting element of a spinal stabilization system. The pedicle screw system further includes: a bone alignment apparatus and a coupling device for at least one of force-locking coupling and form-locking coupling of the bone alignment apparatus and the pedicle screw in an alignment position in which a mobility of the screw head and the screw shaft is reduced from three degrees of freedom of movement in rotation of the screw head supported on the screw shaft in a ball-and-socket joint relationship therewith by at least one degree of freedom of rotation.

20 Claims, 8 Drawing Sheets

(56) References Cited

U.S. PATENT DOCUMENTS

| | | | |
|---|---|---|---|
| 6,660,006 B2* | 12/2003 | Markworth | A61B 17/7086 606/279 |
| 7,799,031 B2* | 9/2010 | Miller | A61B 17/7088 606/279 |
| 7,951,172 B2 | 5/2011 | Chao | |
| 9,480,505 B2* | 11/2016 | Hutchens | A61B 17/7086 |
| 2002/0072752 A1* | 6/2002 | Zucherman | A61B 17/7074 606/99 |
| 2002/0095153 A1* | 7/2002 | Jones | A61B 17/7037 606/86 A |
| 2003/0225408 A1* | 12/2003 | Nichols | A61B 17/7032 606/86 A |
| 2003/0236529 A1* | 12/2003 | Shluzas | A61B 17/7079 606/105 |
| 2004/0147936 A1* | 7/2004 | Rosenberg | A61B 17/7086 606/99 |
| 2004/0249378 A1* | 12/2004 | Saint Martin | A61B 17/7032 606/86 A |
| 2006/0025768 A1* | 2/2006 | Iott | A61B 17/7032 606/86 A |
| 2006/0166534 A1* | 7/2006 | Brumfield | A61B 17/7088 439/179 |
| 2008/0051794 A1* | 2/2008 | Dec | A61B 17/7091 606/250 |
| 2008/0195150 A1* | 8/2008 | Bishop | A61B 17/7037 606/246 |
| 2008/0262318 A1* | 10/2008 | Gorek | A61B 17/0206 600/235 |
| 2010/0030283 A1* | 2/2010 | King | A61B 17/7037 606/86 A |
| 2011/0106174 A1* | 5/2011 | Rezach | A61B 17/7032 606/305 |
| 2011/0263945 A1* | 10/2011 | Peterson | A61B 17/0218 600/213 |
| 2013/0150904 A1 | 6/2013 | Biedermann | |
| 2013/0204308 A1 | 8/2013 | Barry | |
| 2014/0236236 A1 | 8/2014 | Kruger | |
| 2015/0238235 A1* | 8/2015 | Tuten | A61B 17/7077 606/279 |
| 2015/0320468 A1 | 11/2015 | Kruger | |

FOREIGN PATENT DOCUMENTS

| | | |
|---|---|---|
| DE | 102013100574 | 7/2014 |
| WO | 2013134368 | 9/2013 |

* cited by examiner

PEDICLE SCREW SYSTEM AND SPINAL STABILIZATION SYSTEM

CROSS-REFERENCE TO RELATED APPLICATIONS

This application is related to and claims the benefit of priority of German patent application number DE 10 2014 117 176.4, filed Nov. 24, 2014, the contents of which is incorporated by reference herein in its entirety and for all purposes.

FIELD

The present invention relates to pedicle screw systems generally, and more specifically to a pedicle screw system, comprising a pedicle screw having a screw shaft with an external thread and having a screw head supported on the screw shaft in a ball-and-socket joint relationship therewith, which screw head comprises a connecting element receptacle for a connecting element of a spinal stabilization system.

The present invention further relates to spinal stabilization systems generally, and more specifically to a spinal stabilization system comprising at least two bone screws and at least one connecting element capable of being fixed in place on the at least two bone screws.

BACKGROUND

Pedicle screws and spinal stabilization systems of the type described at the outset are known for example from DE 10 2013 100 574 A1. They can be used for example in deformity surgery in order to impart to a deformed spine a desired form and fix it thereinto by appropriate implantation and alignment of pedicle screws. For the alignment of individual malpositioned vertebrae, the forces for the corrective maneuver are introduced into the respective vertebra via the pedicle screws.

In pedicle screw systems which permit top-loading of a connecting element into a corresponding connecting element receptacle on the screw head, i.e. in what are known as "tulip" design systems, an introduction of force is not possible if the pedicle screw is configured in the form of a polyaxial screw. Force introduction is only possible if the screw head is immovable relative to the screw shaft or is, at most, pivotable about a single axis, i.e. if the pedicle screw is what is known as a monoaxial screw. With this design, the screw head is moved in a plane which extends perpendicularly to the axis about which it is pivoted so that in this sense the monoaxial screw can also be referred to as a uniplanar screw. With polyaxial screws, on the other hand, which considerably simplify the insertion of the connecting element, such as a rod, by the screw head being able to be given any desired orientation with respect to the screw shaft, such an introduction of force and correction of a vertebra's alignment is not possible or is possible in only a rudimentary form. In particular, the technique of segmental derotation cannot be applied with polyaxial screws. This technique can only be implemented with the direct introduction of force into the pedicle screw as allowed by the described monoaxial screws in particular.

SUMMARY

In a first aspect of the invention, a pedicle screw system comprises a pedicle screw having a screw shaft with an external thread and having a screw head supported on the screw shaft in a ball-and-socket joint relationship therewith. Said screw head comprises a connecting element receptacle for a connecting element of a spinal stabilization system. Said pedicle screw system further comprises a bone alignment apparatus and a coupling device for at least one of force-locking coupling and form-locking coupling of the bone alignment apparatus and the pedicle screw in an alignment position in which a mobility of the screw head and the screw shaft is reduced from three degrees of freedom of movement in rotation of the screw head supported on the screw shaft in a ball-and-socket joint relationship therewith by at least one degree of freedom of rotation.

In a second aspect of the invention, a spinal stabilization system comprises at least two bone screws and at least one connecting element fixable on the at least two bone screws. At least one of the at least two bone screws is configured in the form of a pedicle screw system which comprises a pedicle screw having a screw shaft with an external thread and having a screw head supported on the screw shaft in a ball-and-socket joint relationship therewith. Said screw head comprises a connecting element receptacle for a connecting element of a spinal stabilization system. Said pedicle screw system further comprises a bone alignment apparatus and a coupling device for at least one of force-locking coupling and form-locking coupling of the bone alignment apparatus and the pedicle screw in an alignment position in which a mobility of the screw head and the screw shaft is reduced from three degrees of freedom of movement in rotation of the screw head supported on the screw shaft in a ball-and-socket joint relationship therewith by at least one degree of freedom of rotation.

BRIEF DESCRIPTION OF THE DRAWING FIGURES

The foregoing summary and the following description may be better understood in conjunction with the drawing figures, of which:

DETAILED DESCRIPTION

Figure 1:
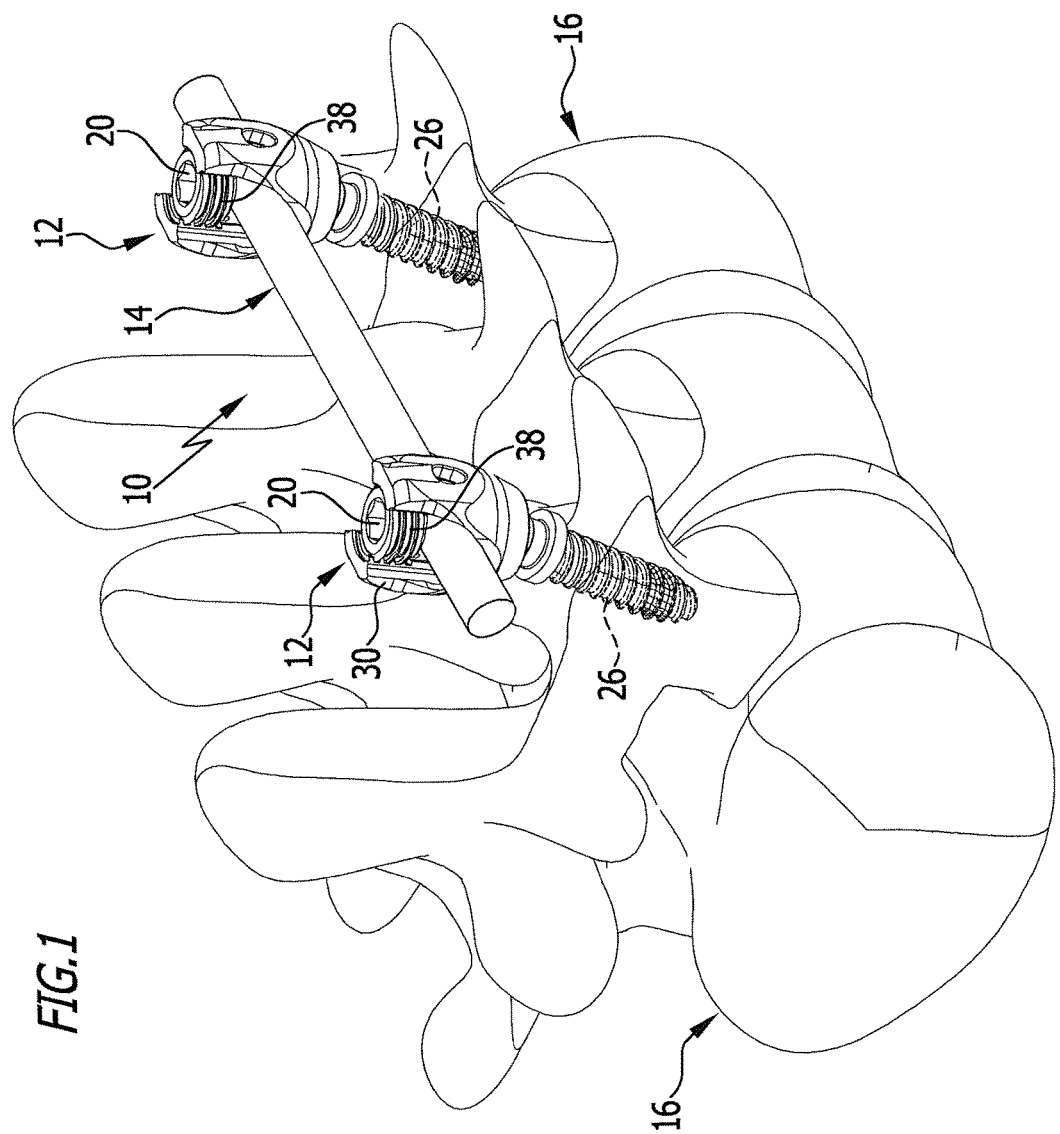
FIG. 1 is a schematic view of a spinal stabilization system comprising two bone screws and a connecting element, shown as being fixed in place on a spine.
Figure 2:
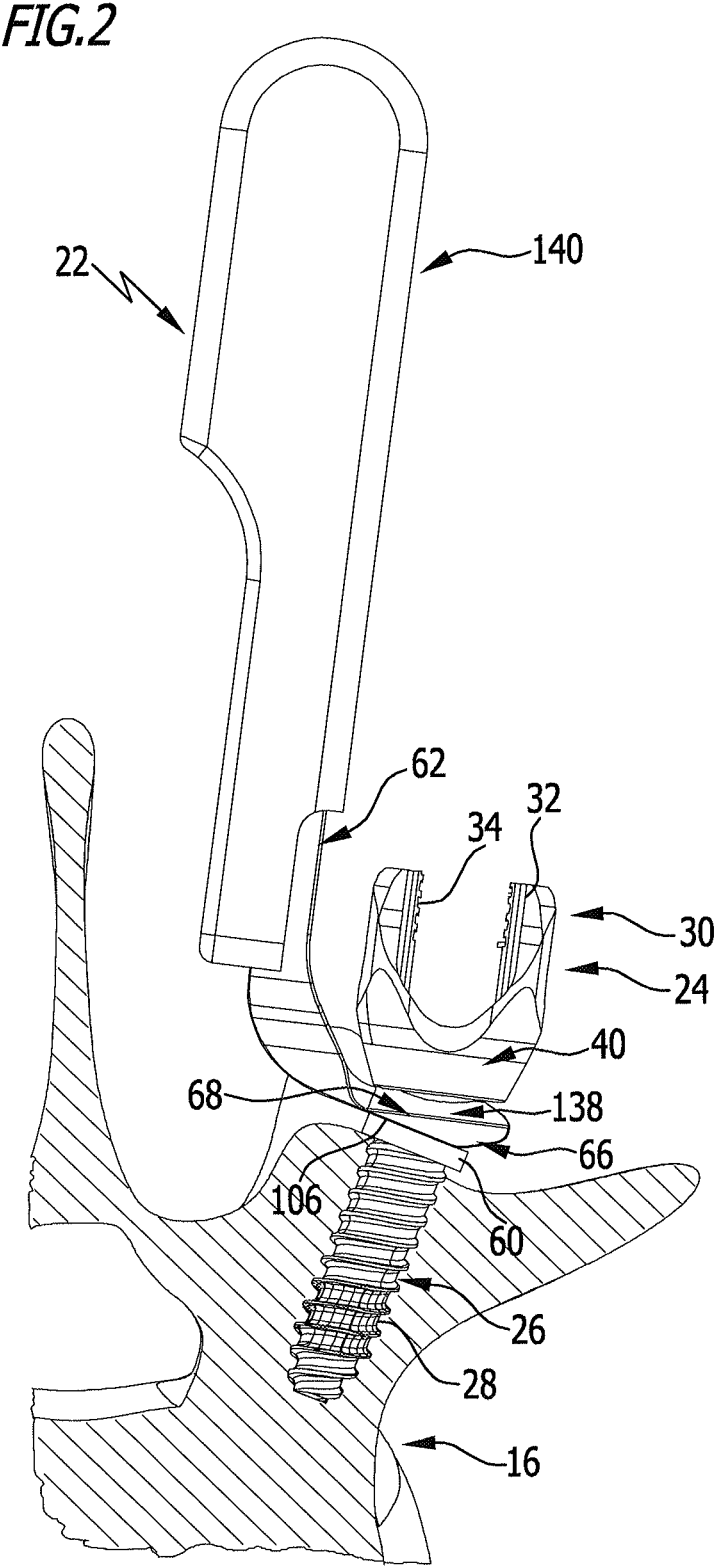
FIG. 2 is a side view of a pedicle screw screwed into a vertebra, shown with a bone alignment apparatus coupled thereto.
Figure 3:
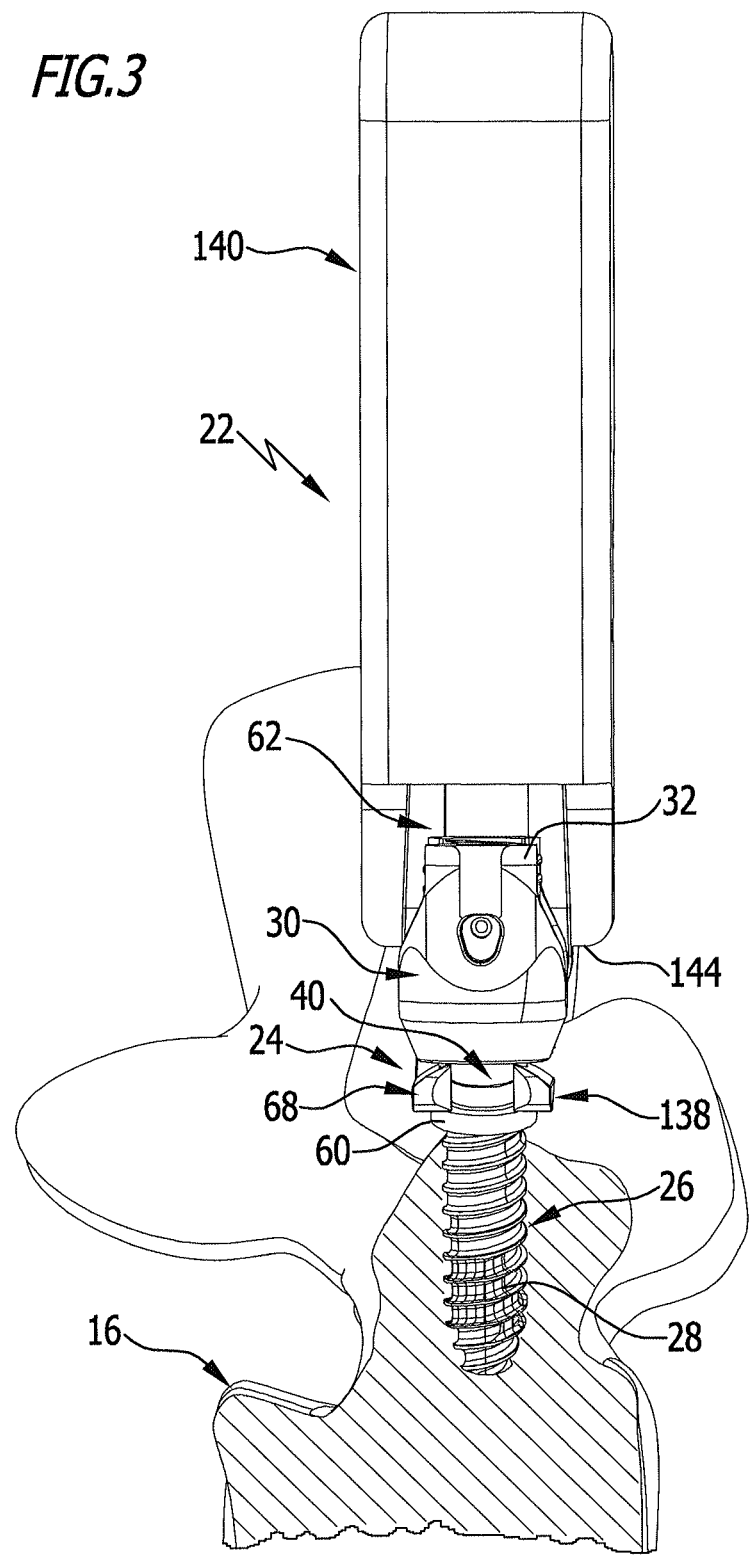
FIG. 3 is another side view of the pedicle screw system illustrated in FIG. 2.
Figure 4:
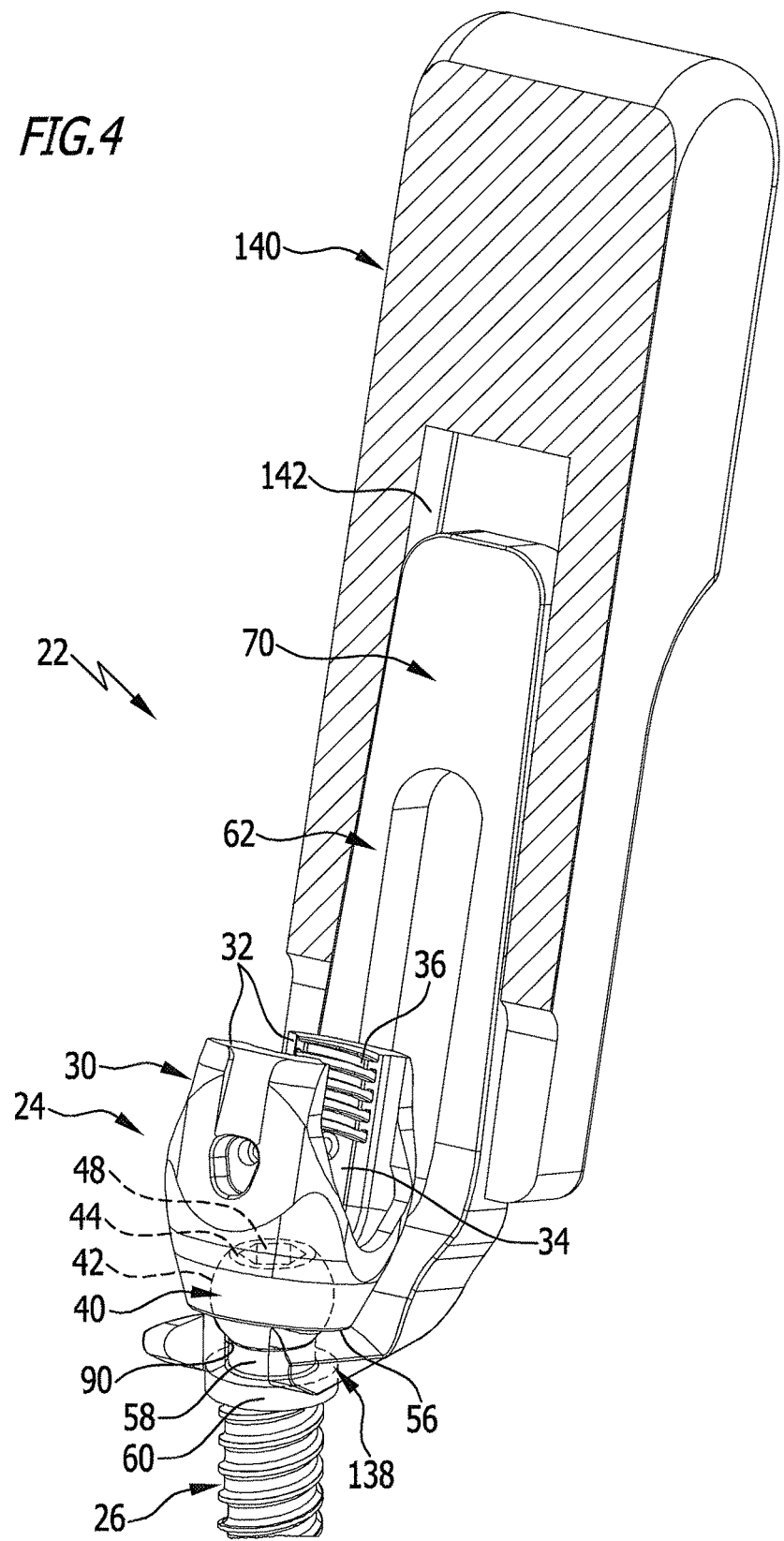
FIG. 4 is a perspective view of the pedicle screw system of FIG. 2.
Figure 5:
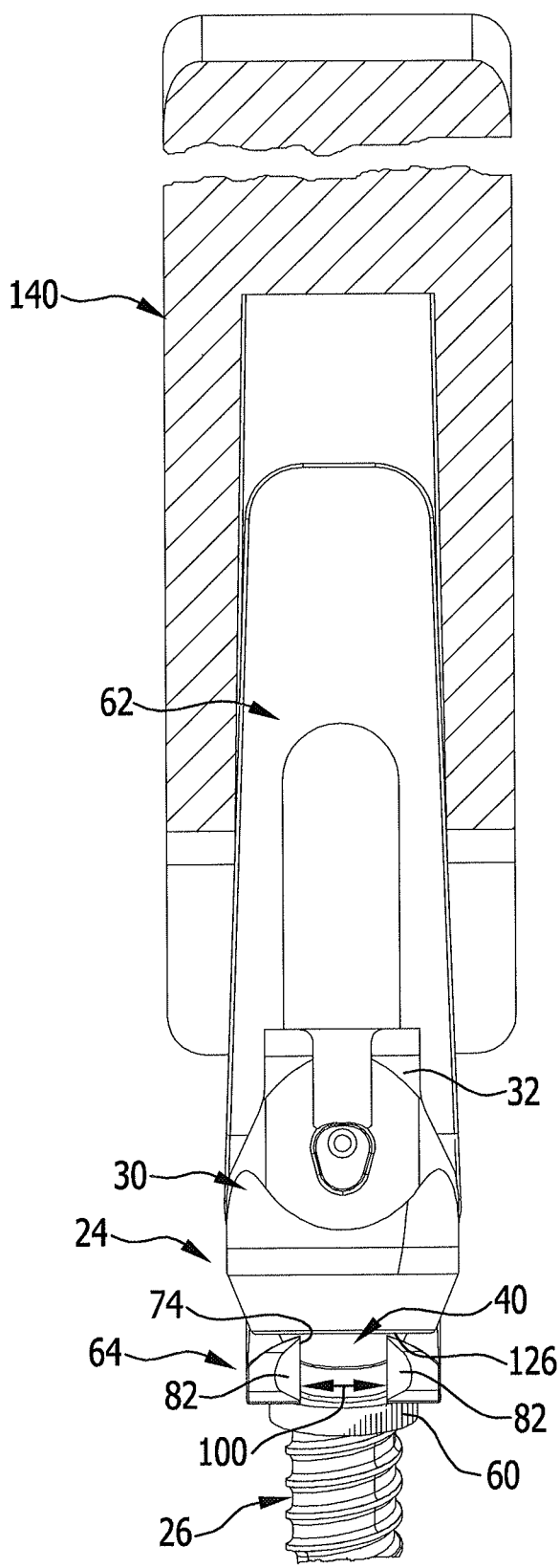
FIG. 5 is the arrangement of FIG. 4 when viewed from the front.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a pedicle screw system, comprising a pedicle screw having a screw shaft with an external thread and having a screw head supported on the screw shaft in a ball-and-socket joint relationship therewith, which screw head comprises a connecting element receptacle for a connecting element of a spinal stabilization system, said pedicle screw system further comprising: a bone alignment apparatus and a coupling device for at least one of force-locking coupling and form-locking coupling of the bone alignment apparatus and the pedicle screw in an alignment position in which a mobility of the screw head and the screw shaft is reduced from three degrees of freedom of movement in rotation of the screw head supported on the screw shaft in a ball-and-socket joint relationship therewith by at least one degree of freedom of rotation.

In particular, the improvement proposed in accordance with the invention enables the surgeon to introduce forces for moving, in particular rotating, deformed vertebrae of a vertebral column via the bone alignment apparatus to the screw shaft directly when the coupling device of the pedicle screw system assumes the alignment position. The proposed pedicle screw system therefore combines, on the one hand, the advantages of polyaxial screws, which enable the screw head to be imparted any desired alignment relative to the screw shaft in order to facilitate insertion of the connecting element into the connecting element receptacle of the screw head, with, on the other hand, and in particular when limiting the degrees of freedom of rotational movement to one rotational degree of freedom, the benefits of a monoaxial screw, which makes possible the introduction of forces to the screw shaft for aligning a vertebral body into which the pedicle screw is screwed. In particular, the number of the originally three degrees of freedom of movement in rotation can be limited to no or one or two degree(s) of freedom of rotational movement.

By the coupling of the bone alignment apparatus and the pedicle screw in the alignment position, an in particular temporary arrangement is provided which in its function corresponds to that of a monoaxial screw. The originally three degrees of freedom of movement allowed by virtue of the ball-and-socket joint interconnection between the screw shaft and the screw head are reduced, by the coupling of the pedicle screw and the bone alignment apparatus in the alignment position, to one degree of freedom of rotational movement. This corresponds to a rotation of the screw shaft and the screw head relative to each other about only a single pivotal axis. In particular, the coupling device allows for an axial and/or a rotationally fixed connection to be established between the bone alignment apparatus and the pedicle screw, thereby enabling, via the bone alignment apparatus, an indirect transfer of force from the bone alignment apparatus to the screw shaft for example.

It is advantageous for the bone alignment apparatus to be configured in the form of a clamping plate or to comprise a clamping plate. By way of example, the clamping plate can be clampingly arranged on the pedicle screw between the screw head and the external thread thereof, thereby to partially block free rotation of the screw head relative to the screw shaft and only permit pivotal movement about just one single pivotal axis as in the case of a monoaxial screw.

It is advantageous for the coupling device to comprise first and second coupling elements which are in force-locking and/or form-locking engagement when in the alignment position and are arranged or formed on the bone alignment apparatus on the one hand and on the pedicle screw on the other hand. With such a coupling device, the bone alignment apparatus can be engaged with the pedicle screw in a simple and safe manner.

Preferably, the first coupling element is configured in the form of a coupling projection and the second coupling element is configured in the form of a coupling receptacle corresponding to the coupling projection. Such coupling elements can be of simple configuration and can be arranged or formed optionally on the pedicle screw or on the bone alignment apparatus.

In particular, in order to prevent or minimize the risk of accidental release of the bone alignment apparatus from the pedicle screw when in the alignment position, it is advantageous for the coupling projection in the alignment position to engage in the coupling receptacle in a form-locking or substantially form-locking manner.

A pedicle screw system that has particular stability can be obtained in particular by configuring the coupling projection in one piece with the screw shaft.

The pedicle screw system is particularly easy to manufacture if the coupling projection is configured in the form of a non-threaded shaft section of the screw shaft. In particular, the non-threaded shaft section can have a circular cross-section or can also have a non-circular cross-section in, for example, the shape of an oval, a rounded-corner polygon or a polygon. It is thus possible for example to enable twisting between the bone alignment apparatus and the pedicle screw by using a circular cross-section or to create a rotationally fixed connection by using a non-circular cross-section.

In accordance with a further preferred embodiment of the invention, provision may be made for the screw shaft to have a joint head and for the screw head to have a joint head receptacle corresponding to the joint head for forming a ball-and-socket joint in cooperation with the joint head. The joint head in cooperation with the joint head receptacle thus provides a simple way of forming a ball-and-socket joint. The joint head can in particular take the form of a sphere or a part of a sphere. The joint head receptacle can be shaped in particular in the form of a hollow-spherical seat corresponding to a ball of a joint.

A simple way of eliminating degrees of freedom of rotation between the screw head and the screw shaft is to arrange the coupling projection between the external thread and the joint head. For example, this provides a simple way of blocking movement of the screw head relative to the screw shaft through the bone alignment apparatus, for example through a clamping connection thereof.

It is advantageous for the coupling device to comprise a stop element on which the bone alignment apparatus is supported when in the alignment position. For example, the stop element can be formed on the screw shaft so that the bone alignment apparatus can be supported on the stop element on the one hand and the screw head on the other hand.

It is advantageous for the bone alignment apparatus to have a stop element contact face which is in contact against the stop element when in the alignment position. In particular, this enables the bone alignment apparatus in the alignment position to be supported on the stop element directly. If the bone alignment apparatus can, on the other hand, be supported on the screw head, then this provides a simple way of limiting the mobility of the screw head relative to the screw shaft.

Preferably, the stop element contact face is of planar or essentially planar configuration. In particular, this configuration enables surface contact with the stop element if the latter presents a planar or essentially planar contact face against which the stop element contact face is in contact when in the alignment position.

It is advantageous for the stop element to have a planar or essentially planar stop face on which the bone alignment apparatus is supported when in the alignment position. Such a stop face is easy to configure and enables surface contact of the bone alignment apparatus against the stop element if the stop element contact face is of planar or essentially planar configuration.

A particularly compact construction of the pedicle screw system can be achieved in particular by the stop element being arranged or formed on the screw shaft.

The screw shaft can be manufactured with particular ease if the stop element is configured in the form of an annular flange. With this configuration, the screw shaft can be manufactured by casting or material-removing machining processes for example.

In accordance with another preferred embodiment of the invention, provision may be made for the stop element to be configured in one piece with the screw shaft or to be connected to the screw shaft in a force-locking manner and/or with a substance-to-substance bond. In particular, the stop element can be connected to the screw shaft by press-fitting, adhesive bonding, soldering or welding. Depending on the type and configuration of the screw shaft and the screw head and the type of the ball-and-socket joint connection therebetween, it may optionally be advantageous for the stop element to be formed in one piece with the screw shaft or to be connected thereto in a force-locking connection or with a substance-to-substance bond.

It is advantageous for an external diameter of the stop element to be larger than a maximum external diameter of the external thread. It is thus possible to ensure that, when in the alignment position, the bone alignment apparatus cannot come into contact with the external thread.

In particular if short screw shafts are used, it is advantageous for the stop element to be directly adjacent to the external thread. In this way, the screw shaft can be screwed into bone as far as the stop element will permit.

It is advantageous for the screw head to have a contact face pointing in a direction towards the external thread, on which the bone alignment apparatus is supported when in the alignment position. In particular, this configuration allows for forces to be transferred from the bone alignment apparatus to the screw head directly or allows for the latter to be acted upon directly for blocking at least two degrees of freedom of rotation of the screw head cooperating with the screw shaft in a ball-and-socket joint relationship.

The screw head is particularly easy to manufacture if the contact face is of planar or essentially planar configuration or has a concavely curved configuration pointing away from the screw head. The contact face is preferably formed such that surface contact with the bone alignment apparatus is possible.

In accordance with another preferred embodiment of the invention, provision may be made for the bone alignment apparatus to have a guide face for predetermining a moving direction for a relative movement between the screw head and the screw shaft, and for the screw head in the alignment position to be in contact against the guide face and to be guided thereon for pivotal movement relative to the screw shaft about a pivotal axis. In particular, the guide face thus provides a simple way of predetermining the desired relative movement between the screw head and the screw shaft, i.e. in particular of only allowing for pivotal movement about a single pivotal axis. This can be achieved in a simple way by shaping the guide face. In particular, the guide face can be convexly curved in a direction pointing towards the screw head. For example, the guide face can extend coaxially with the pivotal axis or the pivotal axis can lie on the guide face.

Preferably, the guide face forms a part of a cylindrical surface. Advantageously, it forms a part of a surface of a right circular cylinder. In particular, a longitudinal axis defined by the right circular cylinder can define the pivotal axis or the pivotal axis can lie on the surface and run parallel to the longitudinal axis of the right circular cylinder.

Advantageously, the pivotal axis runs transversely to a screw shaft longitudinal axis of the screw shaft when in the alignment position. In particular, the pivotal axis can run perpendicularly to the screw shaft longitudinal axis. Of course, the pivotal axis can also extend in an inclined direction relative to a plane extending perpendicularly to the screw shaft longitudinal axis and can enclose an angle of inclination therewith in the range of, for example, approximately 0° to approximately 30°. In particular, this makes it possible for the screw head and the screw shaft in the alignment position to be maintained in the inclined orientation relative to each other at said angle of inclination, while still allowing for pivotal movement about the pivotal axis.

It is advantageous for the bone alignment apparatus to comprise a guide body and for the guide body to comprise the guide face, the stop element contact face and/or one of the coupling elements of the coupling device. A guide body configured in this way can thus perform several functions and, overall, permits the bone alignment apparatus and the pedicle screw system to be implemented in as compact a construction as possible.

Preferably, the coupling receptacle is configured in the form of a recess or through-hole of the bone alignment apparatus. These are easy to manufacture.

Advantageously, the coupling receptacle is configured in the form of a bore. Such a bore is easy to create. In particular, a longitudinal axis of the bore can also predetermine an alignment of the screw head relative to the screw shaft.

In order to further improve the manipulation of the pedicle screw system for a surgeon, it is advantageous for the bone alignment apparatus to comprise a coupling section and a manipulating section and for the coupling section to comprise one of the coupling elements of the coupling device. With such a bone alignment apparatus, it is possible to establish a connection between the coupling section and the pedicle screw when in the alignment position. A surgeon can then grasp the manipulating section either with one hand or with another instrument and can in this way exert a force on the pedicle screw for aligning the screw shaft and hence the vertebra connected therewith in a desired manner.

A particularly simple way of coupling the bone alignment apparatus with the pedicle screw is provided if the bone alignment apparatus is configured such that it is capable of being clipped or latched onto the pedicle screw. Preferably, the coupling section of the bone alignment apparatus is capable of being clipped or latched onto the pedicle screw.

A simple coupling action between the bone alignment apparatus and the pedicle screw can be implemented in particular by the coupling section comprising two clamping legs extending essentially parallel to each other and capable of resiliently moving from a basic position towards one another or away from one another and by the clamping legs being separated one from the other by an introducing slot for introducing the coupling element formed on the pedicle screw. For example, the coupling element formed on the pedicle screw can be introduced in the form of a non-threaded shaft section into the introducing slot so that the latter is somewhat expanded until the coupling element of the pedicle screw comes into engagement, for example snaps into engagement, with the coupling element receptacle of the bone alignment apparatus in the alignment position. The clamping legs in the alignment position can then spring back to the basic position thereof, or they can be retained in the alignment position under some biasing force so that an additional clamping effect of the clamping legs is achieved in order to hold the bone alignment apparatus on the pedicle screw in clamping relationship therewith.

In order to facilitate introducing the coupling element formed on the pedicle screw into the coupling receptacle of the bone alignment apparatus, it is advantageous for a width of the introducing slot to increase in a direction towards a free end of the clamping legs. For example, free ends of the clamping legs can have slide-on faces which facilitate introducing the coupling element formed on the pedicle screw into the introducing slot.

In order for the operation of bringing the bone alignment apparatus into engagement with the pedicle screw to be further facilitated, it is advantageous for the introducing slot to partially extend into the manipulating section. In particular, this enables the configuration of very long clamping legs which then need only undergo a small amount of spreading for coupling the bone alignment apparatus and the pedicle screw together in the alignment position.

In order to couple the bone alignment apparatus with the pedicle screw substantially without imposing any clamping forces thereon, it is advantageous for an internal diameter of the coupling receptacle to be adapted to an external diameter of the non-threaded shaft section.

In accordance with a further preferred embodiment of the invention, provision may be made for the coupling receptacle to define a coupling receptacle longitudinal axis and for the coupling receptacle longitudinal axis to run transversely with respect to the pivotal axis. For example, it can run perpendicularly to the pivotal axis. In particular, the coupling receptacle can be configured such that the coupling receptacle longitudinal axis in the alignment position coincides with a longitudinal axis defined by the screw head and is inclined with respect to the screw shaft longitudinal axis by the above-mentioned angle of inclination.

In particular, in order to enable use of the pedicle screw system in minimally invasive surgical procedures, it is advantageous for the coupling section and the manipulating section to be angled to each other. Preferably, an angle of said angled configuration is in the range of approximately 70° to approximately 110°.

In order for the bone alignment apparatus to be able to be grasped and held in a simple and safe manner, it is advantageous for the manipulating section to comprise a handle portion connecting the two clamping legs together. This allows a surgeon to manipulate the bone alignment apparatus along with the pedicle screw coupled thereto in a simple and safe manner.

It is further advantageous for the pedicle screw system to comprise a plurality of bone alignment apparatuses in which the stop element contact face and a guide face longitudinal axis of the guide face have different alignment angles relative to one another. With such a set of bone alignment apparatuses of the pedicle screw system, a surgeon can in each case select the bone alignment apparatus with which he or she wishes to predetermine a fixed angle of inclination of the screw shaft and the screw head with respect to each other in the alignment position. For example, the set can have angles of inclination in steps of 10° in order to allow for the angle of inclination of the screw shaft and the screw head relative to each other in the alignment position to be predetermined in defined steps, for example with angles of inclination of 0°, 10°, 20° and so forth.

It is advantageous for the bone alignment apparatus to have a screw shaft receptacle in which the screw shaft engages at least partially when in the alignment position. In particular, the screw shaft can extend through the screw shaft receptacle when in the alignment position, i.e. for example project with a distal end thereof from the screw shaft receptacle on the distal side.

The pedicle screw system can be configured in a particularly simple and compact manner if the coupling receptacle defines the screw shaft receptacle.

The invention further relates to a spinal stabilization system comprising at least two bone screws and at least one connecting element fixable on the at least two bone screws, wherein at least one of the at least two bone screws is configured in the form of a pedicle screw system, comprising a pedicle screw having a screw shaft with an external thread and having a screw head supported on the screw shaft in a ball-and-socket joint relationship therewith, which screw head comprises a connecting element receptacle for a connecting element of a spinal stabilization system, said pedicle screw system further comprising: a bone alignment apparatus and a coupling device for at least one of force-locking coupling and form-locking coupling of the bone alignment apparatus and the pedicle screw in an alignment position in which a mobility of the screw head and the screw shaft is reduced from three degrees of freedom of movement in rotation of the screw head supported on the screw shaft in a ball-and-socket joint relationship therewith by at least one degree of freedom of rotation.

In particular, such an improved spinal stabilization system then also includes the advantages described above in connection with preferred embodiments of pedicle screw systems.

FIG. 1 illustrates an example of a spinal stabilization system, designated generally by the reference character 10, said spinal stabilization system 10 comprising two bone screws 12 and a connecting element 14 fixed in place on the two bone screws 12. The bone screws 12 are each fixed in place on a vertebra 16 of a spine 18.

Of course, the spinal stabilization system 10 can also comprise more than two bone screws 12. These can be connected together via one or more connecting elements 14 for example.

FIG. 1 shows an example of a connecting element 14 which takes the form of a round rod. It is also conceivable for the connecting element 14 to take the form of plate-like connecting elements having appropriately configured sections that can be inserted into the connecting element receptacles of the bone screws 12 and can, for example, be fixed in place by a fixation screw 20 in each case.

In principle, the bone screws 12 may be conventional pedicle screws available on the market. It is, however, preferred for at least one of the bone screws 12 to be configured in the form of a pedicle screw system 22 which will be described in detail below.

Each of the pedicle screw systems 22 comprises a pedicle screw 24 having a screw shaft 26 with an external thread 28, for example in the form of a self-tapping bone thread, and having a screw head 30 supported on the screw shaft 26 in a ball-and-socket joint relationship therewith. The screw head 30 has a connecting element receptacle 34 formed between two free legs 32 for receiving the connecting element 14 of the spinal stabilization system 10.

Furthermore, the connecting element receptacle 34 has provided thereon an internal thread 36 of a configuration corresponding to an external thread 38 of the fixation screw 20 so that the fixation screw 20 for fixing in place the connecting element 14 can be screwed, starting from free ends of the legs 32, into the connecting element receptacle 34 in order to fix the connecting element 14 in place on the screw head 30.

To form a ball-and-socket joint 40 between the screw shaft 26 and the screw head 30, a proximal end of the screw shaft 26 is configured in the form of a joint head 42 having a planar end face 44 pointing in a proximal direction, said end face 44 having adjacent thereto a joint head face 46 forming part of a surface of a sphere. Pointing in a proximal direction, a tool element receptacle 48 is formed in the joint head 42, and this can take the form of for example an internal polygon or an internal polygon with rounded corners.

Formed on the screw head 30 is a joint head receptacle 50 in the form of a seat 52 having a configuration corresponding to the joint head 42, said seat 52 opening into a through-hole 54 tapering in internal diameter in a distal direction, said through-hole 54 being formed at a distal end 56 of the screw head 30 and having the screw shaft 26 protruding therefrom distally of the joint head 42.

On the distal side, the joint head 42 is adjoined by a non-threaded shaft section 58 which is bounded by an annular flange 60 on the distal side. The annular flange 60 has an external diameter that is somewhat larger than an external diameter of the joint head 42.

The pedicle screw system 22 further comprises a bone alignment apparatus 62 and a coupling device 64 for force-locking and/or form-locking coupling of the bone alignment apparatus 62 and the pedicle screw 24 in an alignment position as shown in FIGS. 2 to 7 for example.

The bone alignment apparatus 62 comprises a clamping plate 66 which forms a coupling section 68 of the bone alignment apparatus 62. On the proximal side, the coupling section 68 is adjoined by a manipulating section 70.

The coupling section 68 comprises two clamping legs 72 extending essentially parallel to each other and capable of resiliently moving from a basic position towards one another or away from one another, said clamping legs 72 being separated from each other through an introducing slot 74. The introducing slot 74 extends partially into the manipulating section 70.

A proximal end of the bone alignment apparatus 62 forms a handle portion 76 in the form of a connecting plate 78, interconnecting the two clamping legs 72.

A width of the introducing slot 74 increases in a direction towards free ends 80 of the clamping legs 72 so that slide-on faces 82 are formed that are inclined to each other pointing in a distal direction.

The coupling device 64 comprises first and second coupling elements 84 and 86 which are in force-locking and/or form-locking engagement when in the alignment position. They are arranged and formed on the bone alignment apparatus 62 on the one hand and on the pedicle screw 24 on the other hand.

In the exemplary embodiment as represented schematically in the figures, the first coupling element 84 is configured in the form of a coupling projection 88 and the second coupling element 86 is configured in the form of a coupling receptacle 90 corresponding to the coupling projection 88. As is clearly shown in FIGS. 4 and 5 in particular, the coupling projection 88 engages in the coupling receptacle 90 in a form-locking or essentially form-locking manner when in the alignment position.

The coupling projection 88 is configured in one piece with the screw shaft 26, namely in the form of the non-threaded shaft section 58. The coupling projection 88 is thereby arranged between the external thread 28 and the joint head 42.

The coupling receptacle 90 is configured in the form of a through-hole 92, namely as a bore 94. An internal diameter 96 of the bore 94 is adapted to an external diameter 98 of the non-threaded shaft section 58. A width 100 of the introducing slot 74 is smaller than the external diameter 98.

The coupling receptacle 90 defines a coupling receptacle longitudinal axis 102. This runs perpendicularly to a plane 104 which is defined by an underside 106 of the clamping plate 66.

The coupling section 68 and the manipulating section 70 define longitudinal axes 108 and 110 respectively, these being angled to each other at an angle 112. The angle 112 is preferably in a range of about 60° to about 120° and can be about 90° in particular.

In the exemplary embodiment of the bone alignment apparatus 62 as illustrated in the figures, the coupling receptacle 90 forms a screw shaft receptacle 114 through which the screw shaft 26 extends, i.e. in which it engages at least partially, when in the alignment position.

The coupling device 64 further comprises a stop element 116 on which the bone alignment apparatus 62 in the alignment position is supported on the one hand. The underside 106 defines a stop element contact face 118 that is in contact against the stop element 116 when in the alignment position. In the exemplary embodiment shown in the figures, the stop element contact face 118 is of planar configuration.

The stop element 116 has a planar stop face 120 on which the bone alignment apparatus 62 is supported with its stop element contact face 118 when in the alignment position.

The stop element 116 is arranged or formed on the screw shaft 26, namely in the form of the annular flange 60. The stop element 116 is preferably formed in one piece with the screw shaft 26. However, in alternative embodiments, the screw shaft 26 can be connected to the stop element 116 in a force-locking manner and/or with a substance-to-substance bond, such as by press-fitting, adhesive bonding, soldering or welding.

The annular flange 60 is dimensioned such that its external diameter 122 is larger than a maximum external diameter 124 of the external thread 28. In addition, the stop element 116 is directly adjacent to the external thread 28.

Furthermore, the screw head 30 has a contact face 126 pointing in a direction towards the external thread 28, on which the bone alignment apparatus 62 in the alignment position is supported, namely with an upper side 128 of the clamping plate 66 thereof. In the screw head 30 as exemplified in the figures, the contact face 126 is of planar configuration. Alternatively, it may be configured with a concave curvature pointing away from the screw head 30 in a direction towards the external thread 28.

The upper side 128 of the bone alignment apparatus 62 defines a guide face 130 for predetermining a moving direction for a relative movement between the screw head 30 and the screw shaft 26. As is clearly shown in FIG. 7 for example, the screw head 30 in the alignment position is in contact against the guide face 130 and is guided thereon for pivotal movement relative to the screw shaft 26 about a pivotal axis 132.

The guide face 130 is configured with a convex curvature in a direction towards the screw head 30 and can in particular form a part of a cylindrical surface 134, particularly a part of a surface of a right circular cylinder.

Figure 6:
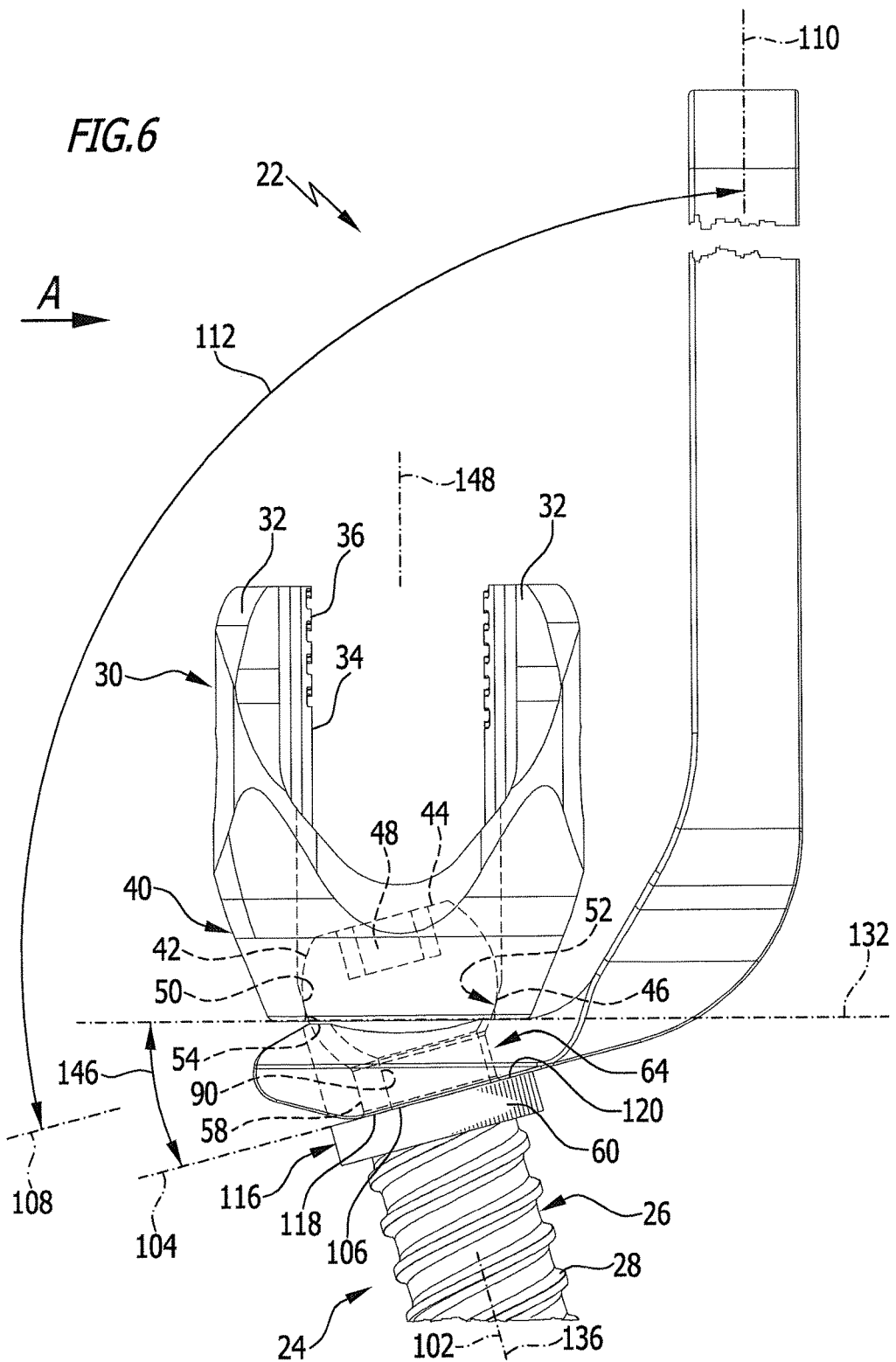
FIG. 6 is a side view of a bone alignment apparatus, shown as being coupled to a pedicle screw.

The pivotal axis 132 is transverse, i.e. perpendicular in the exemplary embodiment illustrated in the figures, to the coupling receptacle longitudinal axis 102. As is shown in FIG. 6 in particular, the pivotal axis 132 is therefore also perpendicular to a screw shaft longitudinal axis 136 of the screw shaft 26.

The clamping plate 66 forms a guide body 138 that comprises the guide face 130, the stop element contact face 118 and the second coupling element 86.

Figure 8:
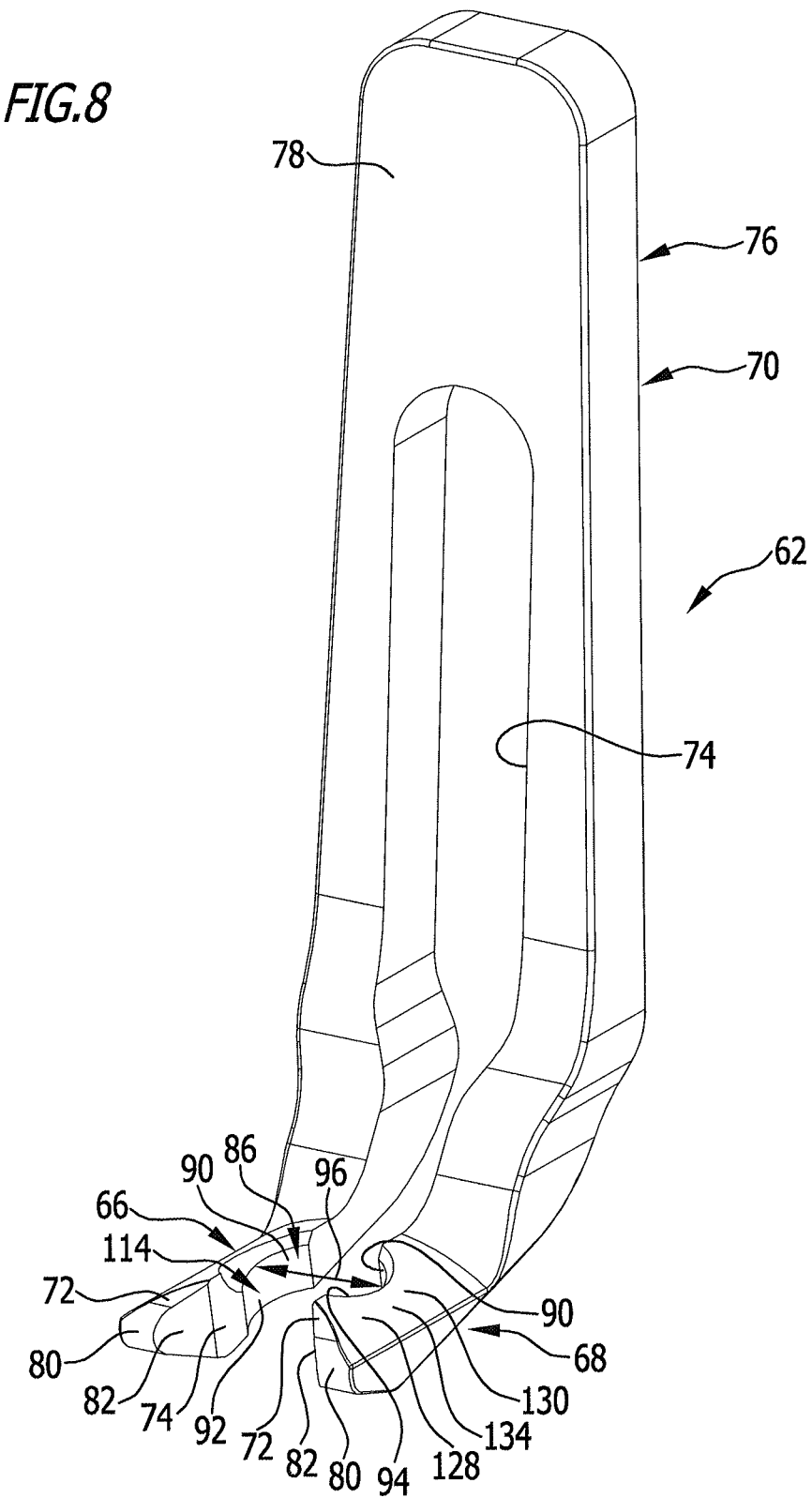
FIG. 8 is a perspective view of the bone alignment apparatus of FIG. 6.

The particular configuration of the bone alignment apparatus 62 makes it possible, due to the particular arrangement and configuration of the introducing slot 74, for the clamping legs 72 to be capable of being resiliently moved from the basic position shown in FIG. 8 towards one another or away from one another.

In order to introduce the coupling projection 88 into the coupling receptacle 90 through the introducing slot 74, the clamping legs 72 are somewhat spread out so that the introducing slot 74, which in the basic position is narrower than the external diameter 98, is somewhat expanded. When the shaft section 58 slides onto the slide-on faces 82, the introducing slot 74 expands and the shaft section 58 can be slid therethrough into the coupling receptacle 90. When the shaft section 58 engages in the coupling receptacle 90, the clamping legs 72 snap or resiliently move back towards one another and surround the shaft section 58 partially. The bone alignment apparatus 62, namely the coupling section 68 thereof, can be clipped or latched onto the pedicle screw 24 in the manner described.

Figure 7:
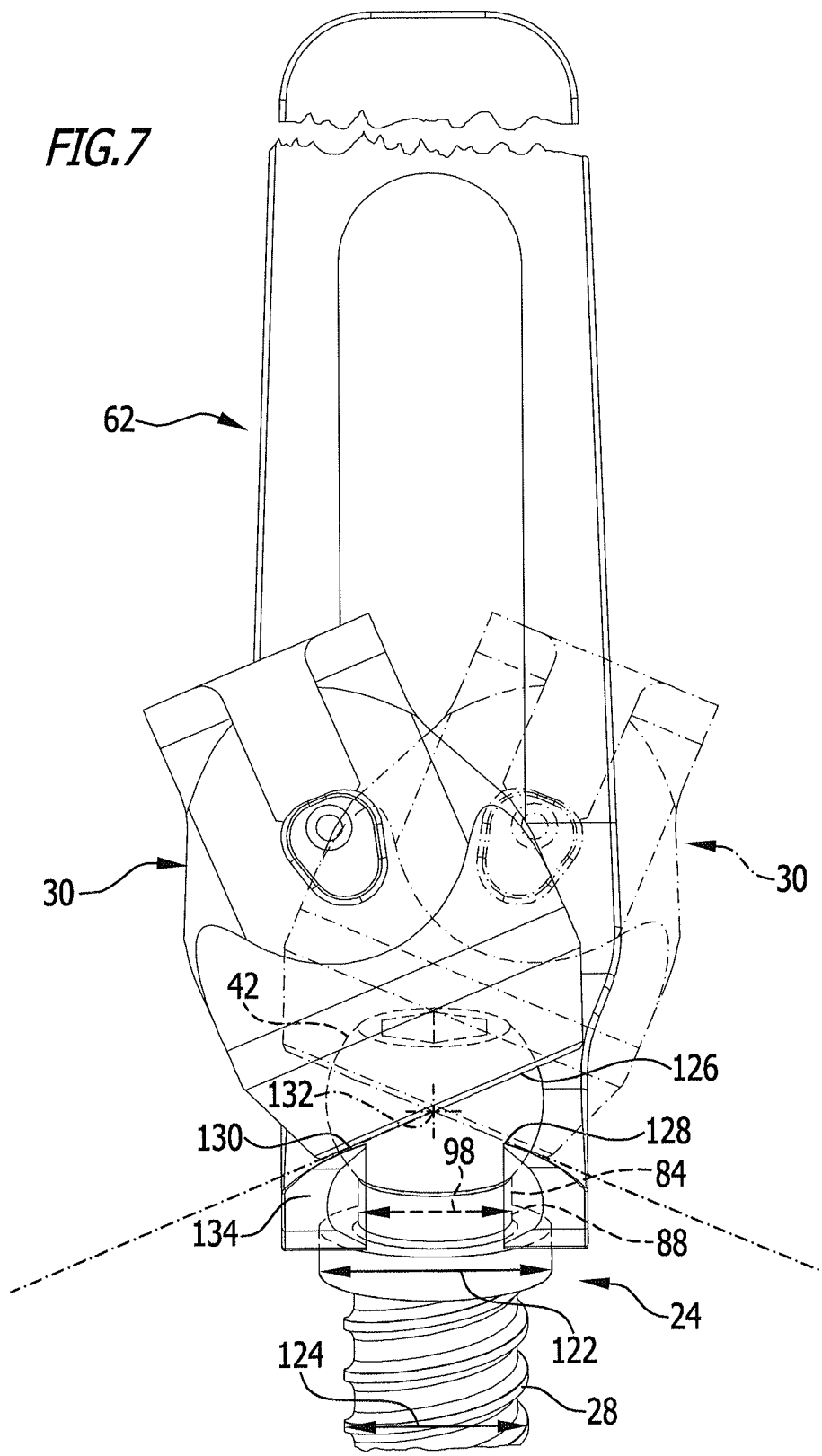
FIG. 7 is a view taken in the direction of arrow A in FIG. 6.

Due to its configuration, the guide face 130 only permits the screw head 30 to pivot relative to the screw shaft 26 exclusively about the pivotal axis 132. The bone alignment apparatus 62 in the alignment position thereby limits the mobility of the screw head 30 and the screw shaft 26 from originally three degrees of freedom of movement in rotation, which are defined by the ball-and-socket joint 40, to just one single degree of freedom of rotation which is defined by the pivotal axis 132. Accordingly, only the pivotal movement about the pivotal axis 132 as shown schematically in FIG. 7 is possible. In this way, the pedicle screw 24 configured as a polyaxial screw, in cooperation with the bone alignment apparatus 62, is practically reduced to the functionality of a monoaxial screw in which the screw head 30 is pivotable relative to the screw shaft 26 solely about the single pivotal axis 132.

In order to prevent accidental release of the bone alignment apparatus 62 from the pedicle screw 24, the pedicle screw system 22 optionally comprises a blocking sleeve 140. This has a receptacle 142 of a configuration corresponding to the manipulating section 70, into which the manipulating section 70 can be slid in a direction parallel to the longitudinal axis 110, as exemplified in FIG. 4.

The receptacle 142 is closed on all sides to a point close to a distal end 144 of the blocking sleeve 140 so that the clamping legs 72 can no longer be pivoted away from one another. The bone alignment apparatus 62 coupled to the pedicle screw 24 can then no longer be released from the pedicle screw 24 without the blocking sleeve 140 being pulled off again from the manipulating section 70 in a proximal direction.

In the exemplary embodiment illustrated in the figures, the upper side 128 of the guide body 138 is inclined relative to the underside 106 by an alignment angle 146. The alignment angle 146 predetermines the inclination of a longitudinal axis 148 of the screw head 30 relative to the screw shaft longitudinal axis 136. Optionally, the pedicle screw system 22 may comprise a plurality of bone alignment apparatuses 62 which differ in the configuration of the guide body 138 such that they have different alignment angles 146. The pedicle screw system 22 can thus comprise a set of bone alignment apparatuses 62 which permit a surgeon to specifically select an alignment of the longitudinal axis 148 and the screw shaft longitudinal axis 136, thereby predetermining for the pedicle screw 24 temporarily forming a monoaxial screw in the alignment position a pivot direction for the screw head 30 thereof.

The described set of bone alignment apparatuses 62 having different alignment angles 146 makes it possible for a surgeon to select an intraoperative adjustment of the pivotal axis 132. A physician can thus influence, by appropriate choice of the bone alignment apparatus 62 having the alignment angle 146 desired by the physician, the position of the screw head 30 after rotation of the vertebra 16 with the aid of the bone alignment apparatus 62, and as a result simplify the insertion of the connecting element 14 in the connecting element receptacle 34 of the pedicle screw 24.

The pedicle screw system 22 makes possible the partial, in particular direction-dependent blocking of the polyaxiality of the pedicle screw 24 by the temporary coupling thereof with the bone alignment apparatus 62 in the alignment position and, optionally, the intraoperative adjustment of an angle between the longitudinal axis 148 and the screw shaft longitudinal axis 136 by appropriate choice of a bone alignment apparatus 62 that presents the desired alignment angle 146. Nevertheless, the possibility still remains for the screw head 30 to be rotated relative to the screw shaft 26 about the longitudinal axis 148 even when in the alignment position.

When full polyaxiality of the pedicle screw 24 is again desired, the bone alignment apparatus 62 is released from the pedicle screw 24 again in the manner described.

The invention claimed is:

1. A pedicle screw system, comprising:
   a pedicle screw having a screw shaft with an external thread and having a screw head supported on the screw shaft in a ball-and-socket joint relationship therewith, which screw head comprises a connecting element receptacle for a connecting element of a spinal stabilization system, said pedicle screw system further comprising:
   a bone alignment apparatus and a coupling device for at least one of force-locking coupling and form-locking coupling of the bone alignment apparatus and the pedicle screw in an alignment position in which a mobility of the screw head and the screw shaft is reduced from three degrees of freedom of movement in rotation of the screw head supported on the screw shaft in a ball-and-socket joint relationship therewith by at least one degree of freedom of rotation, namely from originally three degrees of freedom of movement in rotation to one or two degree(s) of freedom of rotational movement when the bone alignment apparatus is in at least one of force-locking coupling and form-locking coupling with the pedicle screw.

2. The pedicle screw system in accordance with claim 1, wherein the bone alignment apparatus is configured in the form of a clamping plate or comprises a clamping plate.

3. The pedicle screw system in accordance with claim 1, wherein the coupling device comprises first and second coupling elements which are in at least one of force-locking engagement and form-locking engagement when in the alignment position and are arranged or formed on the bone alignment apparatus on the one hand and on the pedicle screw on the other hand.

4. The pedicle screw system in accordance with claim 3, wherein the first coupling element is configured in the form of a coupling projection and wherein the second coupling element is configured in the form of a coupling receptacle corresponding to the coupling projection.

5. The pedicle screw system in accordance with claim 4, wherein the coupling projection at least one of
in the alignment position engages in the coupling receptacle in a form-locking manner or in a substantially form-locking manner
and
is configured in one piece with the screw shaft
and
is configured in the form of a non-threaded shaft section of the screw shaft.

6. The pedicle screw system in accordance with claim 1, wherein the screw shaft has a joint head and wherein the screw head has a joint head receptacle corresponding to the joint head for forming a ball-and-socket joint in cooperation with the joint head.

7. The pedicle screw system in accordance with claim 6, wherein the coupling projection is arranged between the external thread and the joint head.

8. The pedicle screw system in accordance with claim 1, wherein the coupling device comprises a stop element on which the bone alignment apparatus is supported when in the alignment position.

9. The pedicle screw system in accordance with claim 8, wherein at least one of
the bone alignment apparatus has a stop element contact face which is in contact against the stop element when in the alignment position
and
the stop element contact face is of planar or essentially planar configuration.

10. The pedicle screw system in accordance with claim 8, wherein the stop element at least one of
has a planar or essentially planar stop face on which the bone alignment apparatus is supported when in the alignment position
and
is arranged or formed on the screw shaft.

11. The pedicle screw system in accordance with claim 8, wherein the stop element is configured in one piece with the screw shaft or is connected to the screw shaft at least one of in a force-locking manner and with a substance-to-substance bond.

12. The pedicle screw system in accordance with claim 1, wherein at least one of
the screw head has a contact face pointing in a direction towards the external thread, on which the bone alignment apparatus is supported when in the alignment position,
and
the bone alignment apparatus has a guide face for predetermining a moving direction for a relative movement between the screw head and the screw shaft and wherein the screw head in the alignment position is in contact against the guide face and is guided thereon for pivotal movement relative to the screw shaft about a pivotal axis.

13. The pedicle screw system in accordance with claim 12, wherein at least one of the guide face forms a part of a cylindrical surface,
and
the pivotal axis runs transversely, to a screw shaft longitudinal axis of the screw shaft when in the alignment position.

14. The pedicle screw system in accordance with claim 1, wherein the bone alignment apparatus comprises at least one of
a guide body and wherein the guide body comprises at least one of the guide face, the stop element contact face and one of the coupling elements of the coupling device
and
a coupling section and a manipulating section and wherein the coupling section comprises one of the coupling elements of the coupling device.

15. The pedicle screw system in accordance with claim 14, wherein the coupling section comprises two clamping legs extending essentially parallel to each other and resiliently movable from a basic position towards one another or away from one another and wherein the clamping legs are separated one from the other by an introducing slot for introducing the coupling element formed on the pedicle screw.

16. The pedicle screw system in accordance with claim 5, wherein an internal diameter of the coupling receptacle is adapted to an external diameter of the non-threaded shaft section.

17. The pedicle screw system in accordance with claim 12, wherein the coupling receptacle defines a coupling receptacle longitudinal axis and wherein the coupling receptacle longitudinal axis runs transversely with respect to the pivotal axis.

18. The pedicle screw system in accordance with claim 15, said pedicle screw system further comprising a plurality of bone alignment apparatuses in which the stop element contact face and a guide face longitudinal axis of the guide face have different alignment angles relative to one another.

19. The pedicle screw system in accordance with claim 1, wherein the bone alignment apparatus has a screw shaft receptacle in which the screw shaft engages at least partially when in the alignment position.

20. A spinal stabilization system comprising at least two bone screws and at least one connecting element fixable on the at least two bone screws, wherein at least one of the at least two bone screws is configured in the form of a pedicle screw system, comprising a pedicle screw having a screw shaft with an external thread and having a screw head supported on the screw shaft in a ball-and-socket joint relationship therewith, which screw head comprises a connecting element receptacle for a connecting element of a spinal stabilization system, said pedicle screw system further comprising:
a bone alignment apparatus and a coupling device for at least one of force-locking coupling and form-locking coupling of the bone alignment apparatus and the pedicle screw in an alignment position in which a mobility of the screw head and the screw shaft is reduced from three degrees of freedom of movement in rotation of the screw head supported on the screw shaft in a ball-and-socket joint relationship therewith by at least one degree of freedom of rotation, namely from originally three degrees of freedom of movement in rotation to one or two degree(s) of freedom of rotational movement when the bone alignment apparatus is in at least one of force-locking coupling and form-locking coupling with the pedicle screw.

\* \* \* \* \*